(12) United States Patent
Culver et al.

(10) Patent No.: US 6,534,691 B2
(45) Date of Patent: *Mar. 18, 2003

(54) MANUFACTURING PROCESS FOR α-OLEFINS

(75) Inventors: David A. Culver, Salem, NJ (US); Rinaldo S. Schiffino, Wilmington, DE (US); Joel David Citron, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/906,974

(22) Filed: Jul. 17, 2001

(65) Prior Publication Data

US 2002/0016521 A1 Feb. 7, 2002

Related U.S. Application Data

(60) Provisional application No. 60/218,888, filed on Jul. 18, 2000.

(51) Int. Cl.[7] .............................. C07C 2/26; C07C 2/34
(52) U.S. Cl. ...................... 585/527; 585/511; 585/512; 585/513; 585/521; 585/522
(58) Field of Search ................................. 585/511, 512, 585/513, 521, 522, 527

(56) References Cited

U.S. PATENT DOCUMENTS

| 4,020,121 A | 4/1977 | Kister et al. |
| 5,955,555 A | 9/1999 | Bennett ................ 526/133 |
| 6,103,946 A | 9/2000 | Brookhart, III et al. |

FOREIGN PATENT DOCUMENTS

| WO | WO 98/27124 | 6/1998 |
| WO | WO 00/15646 | 3/2000 |

OTHER PUBLICATIONS

I. Kroschwitz, et al., Kirk–Othmer Encyclopedia of Chemical Technology, 4th Ed., vol. 17, John Wiley & Sons, New York, p. 839–858.

*Primary Examiner*—Thuan D. Dang

(57) ABSTRACT

An efficient manufacturing process for α-olefins using certain iron containing ethylene oligomerization catalysts, comprises one or more liquid full reactors which are approximately at the bubble point of reacting ethylene, and optionally a final reactor which is at a lower pressure than the first reactor, both operating under other specified conditions. This process minimizes both the capital and operating costs for the plant. The α-olefins produced are useful as monomers for polymers and as chemical intermediates, for example for making detergents.

14 Claims, 1 Drawing Sheet

MANUFACTURING PROCESS FOR α-OLEFINS

CROSS-REFERENCE TO RELATED APPLICATION

This application claims priority under 35 U.S.C. §119 from U.S. Provisional Application Ser. No. 60/218,888 (filed Jul. 18, 2000), which is incorporated by reference herein for all purposes as if fully set forth.

FIELD OF THE INVENTION

An efficient manufacturing process for α-olefins using certain iron containing ethylene oligomerization catalysts, comprises one or more liquid full reactors which are approximately at the bubble point of reacting ethylene, and optionally a final reactor to which no ethylene is fed, both operating under other specified conditions.

TECHNICAL BACKGROUND

α-Olefins are important items of commerce, billions of kilograms being manufactured yearly. They are useful as monomers for (co)polymerizations and as chemical intermediates for the manufacture of many other materials, for example detergents and surfactants. Presently most α-olefins are made by the catalyzed oligomerization of ethylene by various catalysts, especially certain nickel complexes or aluminum alkyls, see for instance U.S. Pat. No. 4,020,121 and I. Kroschwitz, et al., Ed., *Kirk-Othmer Encyclopedia of Chemical Technology*, 4$^{th}$ Ed., Vol. 17, John Wiley & Sons, New York, pp. 839–858. Depending on the catalyst used and the product distribution desired various processes are used, but they tend to operate at high pressures, and/or high temperatures, and/or have large recycle streams, and/or be complex (for example recycle of catalyst streams), all of which increases the capital cost of the manufacturing plant and/or increases plant operating costs, both of course undesirable. Therefore better processes for making α-olefins are of commercial interest.

Recently, as reported in U.S. Pat. No. 5,955,555 and U.S. Pat. No. 6,103,946, both of which are hereby incorporated by reference herein for all purposes as if fully set forth, it has been found that iron complexes of certain tridentate ligands are excellent catalysts for the production of α-olefins from ethylene. Described herein is a manufacturing process for α-olefins which is especially useful with such catalysts. This process results in lower capital costs for the manufacturing plant and/or lower operating costs for the plant than is found in other processes.

SUMMARY OF THE INVENTION

This invention concerns a process for the production of a linear α-olefin product, comprising the step of contacting, in a continuous stirred tank reactor or its equivalent, process ingredients comprising an active ethylene oligomerization catalyst composition, ethylene and a solvent, at a temperature of from about 35° C. to about 80° C., and at a pressure such that the continuous stirred tank reactor or its equivalent is essentially single phase liquid full, wherein the active ethylene oligomerization catalyst comprises an iron complex of a compound of the formula

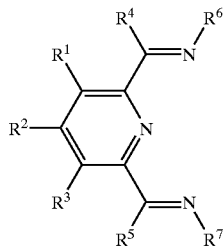

wherein:

$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently a substituted aryl having a first ring atom bound to the imino nitrogen, provided that:

in $R^6$, a second ring atom adjacent to said first ring atom is bound to a halogen, a primary carbon group, a secondary carbon group or a tertiary carbon group; and further provided that in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom.

These and other features and advantages of the present invention will be more readily understood by those of ordinary skill in the art from a reading of the following detailed description. It is to be appreciated that certain features of the invention which are, for clarity, described below in the context of separate embodiments, may also be provided in combination in a single embodiment. Conversely, various features of the invention which are, for brevity, described in the context of a single embodiment, may also be provided separately or in any subcombination.

DETAILED DESCRIPTION OF THE PREFERRED EMBODIMENTS

Figure 1:
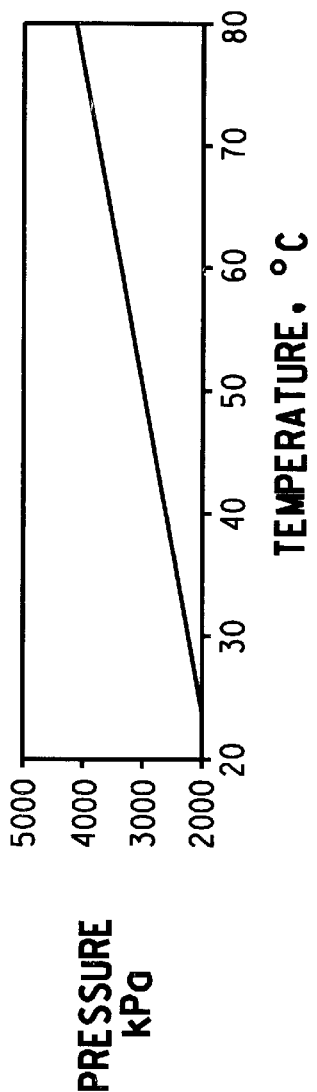
FIG. 1 is a graph of temperature (0° C.) vs. bubble point pressure (in MPa) of ethylene and a mixture of α-olefins typically obtained in the process of the present invention.

Herein, certain terms are used. Some of them are:

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups (and alkyl groups) herein contain 1 to about 30 carbon atoms.

By "substituted hydrocarbyl" herein is meant a hydrocarbyl group that contains one or more substituent groups which are inert under the process conditions to which the compound containing these groups is subjected (e.g., an inert functional group, see below). The substituent groups also do not substantially detrimentally interfere with the oligomerization process or operation of the oligomerization catalyst system. If not otherwise.stated, it is preferred that substituted hydrocarbyl groups herein contain 1 to 30 about 30 carbon atoms. Included in the meaning of "substituted" are rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group, other than hydrocarbyl or substituted hydrocarbyl, which is inert under the process conditions to which the compound containing the group is subjected. The functional groups also do not substantially deleteriously interfere with any process described herein that the compound in which they are present may take part in. Examples of functional groups include halo (fluoro, chloro, bromo and iodo), and ether such as —OR$^{50}$ wherein R$^{50}$ is hydrocarbyl or substituted hydrocarbyl. In cases in which the functional group may be near a transition metal atom, the functional group alone should not coordinate to the metal atom more strongly than the groups in those compounds that are shown as coordinating to the metal atom, that is they should not displace the desired coordinating group.

By a "cocatalyst" or a "catalyst activator" is meant one or more compounds that react with a transition metal compound to form an activated catalyst species. One such catalyst activator is an "alkyl aluminum compound" which, herein, is meant a compound in which at least one alkyl group is bound to an aluminum atom. Other groups such as, for example, alkoxide, hydride and halogen may also be bound to aluminum atoms in the compound.

By a "linear α-olefin product" is meant a composition predominantly comprising a compound (or mixture of compounds) of the formula H(CH$_2$CH$_2$)$_q$CH=CH$_2$ wherein q is an integer of 1 to about 18. In most cases, the linear α-olefin product of the present process will be a mixture of compounds having differing values of q of from 1 to 18, with a minor amount of compounds having q values of more than 18. Preferably less than 50 weight percent, and more preferably less than 20 weight percent, of the product will have q values over 18. The product may further contain small amounts (preferably less than 30 weight percent, more preferably less than 10 weight percent, and especially preferably less than 2 weight percent) of other types of compounds such as alkanes, branched alkenes, dienes and/or internal olefins.

By a "primary carbon group" herein is meant a group of the formula —CH$_2$—, wherein the free valence—is to any other atom, and the bond represented by the solid line is to a ring atom of a substituted aryl to which the primary carbon group is attached. Thus the free valence—may be bonded to a hydrogen atom, a halogen atom, a carbon atom, an oxygen atom, a sulfur atom, etc. In other words, the free valence—may be to hydrogen, hydrocarbyl, substituted hydrocarbyl or a functional group. Examples of primary carbon groups include —CH$_3$, —CH$_2$CH(CH$_3$)$_2$, —CH$_2$Cl, —CH$_2$C$_6$H$_5$, —OCH$_3$ and —CH$_2$OCH$_3$.

By a "secondary carbon group" is meant the group

wherein the bond represented by the solid line is to a ring atom of a substituted aryl to which the secondary carbon, group is attached, and both free bonds represented by the dashed lines are to an atom or atoms other than hydrogen. These atoms or groups may be the same or different. In other words the free valences represented by the dashed lines may be hydrocarbyl, substituted hydrocarbyl or inert functional groups. Examples of secondary carbon groups include —CH(CH$_3$)$_2$, —CHCl$_2$, —CH(C$_6$H$_5$)$_2$, cyclohexyl, —CH(CH$_3$)OCH$_3$, and —CH=CCH$_3$.

By a "tertiary carbon group" is meant a group of the formula

wherein the bond represented by the solid line is to a ring atom of a substituted aryl to which the tertiary carbon group is attached, and the three free bonds represented by the dashed lines are to an atom or atoms other than hydrogen. In other words, the bonds represented by the dashed lines are to hydrocarbyl, substituted hydrocarbyl or inert functional groups. Examples of tetiary carbon groups include —C(CH$_3$)$_3$, —C(C$_6$H$_5$)$_3$, —CCl$_3$, —CF$_3$, —C(CH$_3$)$_2$OCH$_3$, —C≡CH, —C(CH$_3$)$_2$CH=CH$_2$, aryl and substituted aryl such as phenyl and 1-adamantyl.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By "essentially single phase liquid full" herein is meant that at least 95 volume percent of the reactor volume is occupied by a liquid that is a single phase. Small amounts of the reactor volume may be taken up by gas, for example ethylene may be added to the reactor as a gas, which dissolves rapidly under the process conditions. Nevertheless, some small amount of dissolving ethylene gas may be present. Not counted in the reactor volume is any solid resuiting from fouling of the reactor.

By a "bubble point" herein is meant the minimum pressure that must be exerted on the process ingredients to keep all of the ingredients, including ethylene, in the process in the liquid phase (i.e., dissolved). The bubble point pressure will vary with the temperature of the process and the composition of the liquid phase. For example, as the temperature is raised, the minimum pressure needed to maintain a liquid phase (including ethylene) without an ethylene gas phase will increase, and vice versa. The bubble point pressure also changes with the composition of the liquid medium. The bubble point may be measured under various conditions using a pressure cell with a viewport to determine the minimum pressure which, under a given set of conditions, the ethylene gas phase "disappears". Specific techniques that are useful for measuring bubble points will be found in A. Y. Dandekar, et al., *Ind. Eng. Chem. Res.*, vol. 39, p. 2586–2591 (2000); WO98/45691, and S. Raham, et al., *J. Pet. Sci. Eng.*, vol. 14, p. 25–34 (1995), all of which are hereby incorporated by reference herein for all purposes as if fully set forth.

By a "first ring atom in $R^6$ and $R^7$ bound to an imino nitrogen atom" is meant the ring atom in these groups bound to an imino nitrogen shown in (I), for example

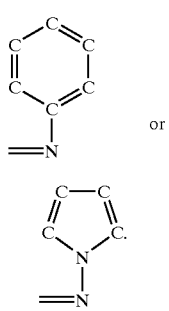

(II)

or (III)

The atoms shown in the 1-position in the rings in (II) and (III) are the first ring atoms bound to an imino carbon atom (other groups which may be substituted on the aryl groups are not shown). Ring atoms adjacent to the first ring atoms are shown, for example, in (IV) and (V), where the open valencies to these adjacent atoms are shown by dashed lines (the 2,6-positions; in (IV) and the 2,5-positions in (V)).

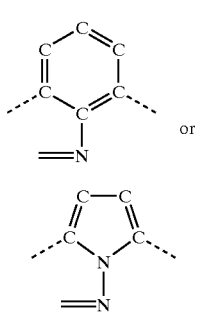

(IV)

or (V)

In one preferred embodiment of (I), $R^6$ is

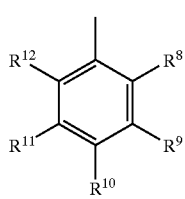

(VI)

and $R^7$ is

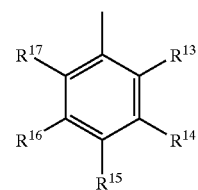

(VII)

wherein:
$R^8$ is a halogen, a primary carbon group, a secondary carbon group or a tertiary carbon group; and
$R^9$, $R^{10}$, $R^{11}$, $R^{14}$, $R^{15}$, $R^{16}$ and $R^{17}$ are each independently hydrogen, hydrocarbyl, substituted hydrocarbyl or a functional group; provided that:
when $R^8$ is a halogen or primary carbon group none, one or two of $R^{12}$, $R^{13}$ and $R^{17}$ are a halogen or a primary carbon group, with the remainder of $R^{12}$, $R^{13}$ and $R^{17}$ being hydrogen; or
when $R^8$ is a secondary carbon group, none or one of $R^{12}$, $R^{13}$ and $R^{17}$ is a halogen, a primary carbon group or a secondary carbon group, with the remainder of $R^{12}$, $R^{13}$ and $R^{17}$ being hydrogen; or
when $R^8$ is a tertiary carbon group, none or one of $R^{12}$, $R^{13}$ and $R^{17}$ is tertiary carbon group, with the remainder of $R^{12}$, $R^{13}$ and $R^{17}$ being hydrogen;
and further provided that any two of $R^8$, $R^9$, $R^{10}$, $R^{11}$, $R^{12}$, $R^{13}$, $R^{14}$ $R^{15}$, $R^{16}$ and $R^{17}$ vicinal to one another, taken together may form a ring.

In the above formulas (VI) and (VII), $R^8$ corresponds to the second ring atom adjacent to the first ring atom bound to the imino nitrogen, and $R^{12}$, $R^{13}$ and $R^{17}$ correspond to the other ring atoms adjacent to the first ring atom.

In compounds (I) containing (VI) and (VII), it is particularly preferred that:
if $R^8$ is a primary carbon group, $R^{13}$ is a primary carbon group, and $R^{12}$ and $R^{17}$ are hydrogen; or
if $R^8$ is a secondary carbon group, $R^{13}$ is a primary carbon group or a secondary carbon group, more preferably a secondary carbon group, and $R^{12}$ and $R^{17}$ are hydrogen; or
if $R^8$ is a tertiary carbon group (more preferably a trihalo tertiary carbon group such as a trihalomethyl), $R^{13}$ is a tertiary carbon group (more preferably a trihalotertiary group such as a trihalomethyl), and $R^{12}$ and $R^{17}$ are hydrogen; or
if $R^8$ is a halogen, $R^{13}$ is a halogen, and $R^{12}$ and $R^{17}$ are hydrogen.

In all specific preferred compounds (I) in which (VI) and (VII) appear, it is preferred that $R^1$, $R^2$ and $R^3$ are hydrogen; and/or $R^4$ and $R^5$ are methyl. It is further preferred that:
$R^9$, $R^{10}$, $R^{11}$, $R^{12}$, $R^{14}$, $R^{15}$, $R^{16}$ and $R^{17}$ are all hydrogen; $R^{13}$ is methyl; and $R^8$ is a primary carbon group, more preferable methyl; or
$R^9$, $R^{10}$, $R^{11}$, $R^{12}$, $R^{14}$, $R^{15}$, $R^{16}$ and $R^{17}$ are all hydrogen; $R^{13}$ is ethyl; and $R^8$ is a primary carbon group, more preferably ethyl; or
$R^9$, $R^{10}$, $R^{11}$, $R^{12}$, $R^{14}$, $R^{15}$, $R^{16}$ and $R^{17}$ are all hydrogen; $R^{13}$ is isopropyl; and $R^8$ is a primary carbon group, more preferably isopropyl; or
$R^9$, $R^{10}$, $R^{11}$, $R^{12}$, $R^{14}$, $R^{15}$, $R^{16}$ and $R^{17}$ are all hydrogen; $R^{13}$ is n-propyl; and $R^8$ is a primary carbon group, more preferably n-propyl; or $R^9$, $R^{10}$, $R^{11}$, $R^{12}$, $R^{14}$, $R^{15}$, $R^{16}$ and $R^{17}$ are all hydrogen; $R^{13}$ is chloro; and $R^8$ is a halogen, more preferably chloro; or $R^9$, $R^{10}$, $R^{11}$, $R^{12}$, $R^{14}$, $R^{15}$, $R^{16}$ and $R^{17}$ are all hydrogen; $R^{13}$ is trihalomethyl, more preferably trifluoromethyl; and $R^8$ is a trialomethyl, more preferably trifluoromethyl.

In another preferred embodiment of (I), $R^6$ and $R^7$ are, respectively

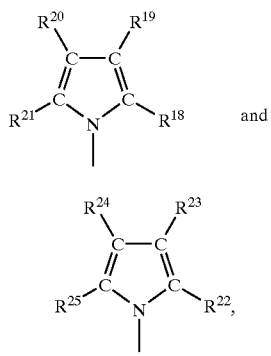

wherein:

$R^{18}$ is a halogen, a primary carbon group, a secondary carbon group or a tertiary carbon group; and $R^{19}$, $R^{20}$, $R^{23}$ and $R^{24}$ are each independently hydrogen, hydrocarbyl, substituted hydrocarbyl or a functional group; Provided that:

when $R^{18}$ is a halogen or primary carbon group none, one or two of $R^{21}$, $R^{22}$ and $R^{25}$ are a halogen or a primary carbon group, with the remainder of $R^{21}$, $R^{22}$ and $R^{25}$ being hydrogen; or when $R^{18}$ is a secondary carbon group, none or one of $R^{21}$, $R^{22}$ and $R^{25}$ is a halogen, a primary carbon group or a secondary carbon group, with the remainder of $R^{21}$, $R^{22}$ and $R^{25}$ being hydrogen;

when $R^{18}$ is a tertiary carbon group, none or one of $R^{21}$, $R^{22}$ and $R^{25}$ is a tertiary carbon group, with the remainder of $R^{21}$, $R^{22}$ and $R^{25}$ being hydrogen;

and further provided that any two of $R^{18}$, $R^{19}$, $R^{20}$, $R^{21}$, $R^{22}$, $R^{23}$, $R^{24}$ and $R^{25}$ vicinal to one another, taken together may form a ring.

In the above formulas (VIII) and (IX), $R^{18}$ corresponds to the second ring atom adjacent to the first ring atom bound to the imino nitrogen, and $R^{21}$, $R^{22}$ and $R^{25}$ correspond to the other ring atoms adjacent to the first ring atom.

In compounds (I) containing (VIII) and (IX), it is particularly preferred that:

if $R^{18}$ is a primary carbon group, $R^{22}$ is a primary carbon group, and $R^{21}$ and $R^{25}$ are hydrogen; or if $R^{18}$ is a secondary carbon group, $R^{22}$ is a primary carbon group or a secondary carbon group, more preferably a secondary carbon group, and $R^{21}$ and $R^{25}$ are hydrogen; or if $R^{18}$ is a tertiary carbon group (more preferably a trihalo tertiary carbon group such as a trihalomethyl), $R^{22}$ is a tertiary carbon group (more preferably a trihalotertiary group such as a trihalomethyl), and $R^{21}$ and $R^{25}$ are hydrogen; or if $R^{18}$ is a halogen, $R^{22}$ is a halogen, and $R^{21}$ and $R^{25}$ are hydrogen.

In all specific preferred compounds (I) in which (VIII) and (IX) appear, it is preferred that $R^1$, $R^2$ and $R^3$ are hydrogen; and/or $R^4$ and $R^5$ are methyl. It is further preferred that:

$R^{19}$, $R^{20}$, $R^{21}$, $R^{23}$ and $R^{24}$ are all hydrogen; $R^{22}$ is methyl; and $R^{18}$ is a primary carbon group, more preferably methyl; or $R^{19}$, $R^{20}$, $R^{21}$, $R^{23}$ and $R^{24}$ are all hydrogen; $R^{22}$ is ethyl; and $R^{18}$ is a primary carbon group, more preferably ethyl; or $R^{19}$, $R^{20}$, $R^{21}$, $R^{23}$ and $R^{24}$ are all hydrogen; $R^{22}$ is isopropyl; and $R^{18}$ is a primary carbon group, more preferably isopropyl; or $R^{19}$, $R^{20}$, $R^{21}$, $R^{23}$ and $R^{24}$ are all hydrogen; $R^{22}$ is n-propyl; and $R^{18}$ is a primary carbon group, more preferably n-propyl; or $R^{19}$, $R^{20}$, $R^{21}$, $R^{23}$ and $R^{24}$ are all hydrogen; $R^{22}$ is chloro or bromo; and $R^{18}$ is a halogen, more preferably chloro or bromo.

The active oligomerization catalyst may be prepared by a variety of methods, see for instance previously incorporated U.S. Pat. No. 5,955,555 and U.S. Pat. No. 6,103,946, as well as U.S. Pat. No. 6,232,259 and WO00/08034, both of which are also incorporated by reference herein for all purposes as if fully set forth.

Where a cocatalyst such as an alkylaluminum compound is required for the active catalyst species, an iron complex of (I), such as a complex of (I) with $FeCl_2$, may be reacted with an alkylaluminum compound, preferably an aluminoxane such as methylaluminoxane, to form an active ethylene oligomerization species. The ratio of aluminum (as alkylaluminum compound) to iron (as a complex) in the oligomerization may be about 10 to about 1000.

The catalyst used in the process of the present invention may be unsupported, or may be supported on any one of a number of well-known substrates such as disclosed in the previously incorporated references. Preferably, however, the catalyst is used in unsupported form.

In the process described herein, as in most chemical manufacturing processes, there is often a balance that is struck between initial capital cost of the manufacturing plant and the operating cost of making the desired product. The process described herein strikes a balance between these two factors which results in exceptionally low manufacturing costs for α-olefins. Within the parameters described herein, small changes can be made to further optimize costs based on various factors, such as the cost of ethylene, local cost of energy, etc.

By a "continuous stirred tank reactor or its equivalent" herein is meant a continuous stirred tank reactor ("CSTR") as is understood by the person skilled in the art plus those reactor configuration considered functionally equivalent thereto.

The standard CSTR comprises a stirred tank with inlets for the catalyst component(s), any recycle α-olefins (solvent) or other solvent and ethylene, and an outlet for the product stream. CSTRs are well known in the art, see for instance J. I. Kroschwitz, et al., Ed., *Kirk-Othmer Encyclopedia of Chemical Technology*, 4$^{th}$ Ed., Vol. 20, John Wiley & Sons, New York, 1996, pp. 1007–1059, which is incorporated herein by reference for all purposes as if fully set forth.

As indicated above, functional equivalents for a CSTR may also be used, for example a circulating loop reactor in which the ingredients are essentially uniform throughout the loop. Such functional equivalents are well-known to, or can be readily determined by, those of ordinary skilled in the relevant art.

More than one CSTR (or equivalent) may be used in series, for example to avoid the installation of very large reactors which may be more expensive than two smaller reactors in series (a preferred configuration), or to help provide enough cooling capacity for the reaction system (see below).

The reaction is run at a pressure such that the process ingredients (catalyst, solvent, ethylene and products) are essentially a single phase liquid so that the reactor is essentially single phase liquid full. Preferably, this ranges from a pressure above the bubble point pressure, to below 2 times the bubble point pressure, but not to exceed the critical pressure of ethylene. By doing so, the reactor(s) used herein are operated essentially single-phase liquid full. This makes the most efficient use of the volume of the reactor, in this instance all of the reactor volume is used to produce α-olefins. The ethylene may be introduced into the reactor as a gas at the bubble point or a higher pressure through sparge or dip tubes, sparge rings, or the like, which are known in the art. While small amounts (<5 volume present of the reactor) of ethylene bubbles may be present while the gas is dissolving, this is still considered liquid full herein.

The process is run in the liquid phase in a "solvent". The solvent may be a liquid, such as an inert organic liquid, which does not react to any significant degree with any of the process components. Preferably the solvent is the reaction product of the oligomerization itself, one or more α-olefins, preferably the mixture or partial mixture (for instance less lower boiling α-olefins such as 1-butene) of α-olefins produced by the process. To start the process a separate solvent may be used initially with the liquid medium eventually being mostly the α-olefins, or one or more α-olefins may be used initially. Some of the product stream α-olefins may be recycled back to the reactor to provide extra "solvent" for the process (particularly the ethylene oligomerization components) or none of the α-olefins maybe recycled.

The process temperature, usually between about 35° C. and about 80° C., more preferably between about 35° C. and about 75° C., affects the cost of manufacture of the α-olefins in several ways. The higher the temperature the less cooling that has to be applied to the reactor(s) and/or the higher the temperature of the coolant used to maintain the desired temperature. Less cooling and/or higher coolant temperature generally lowers cost. The decay of the active oligomerization catalyst increases with increasing temperature. It is found that maximum volumetric production of α-olefins coupled with good absolute productivity of the catalyst usually occurs in the range of about 45° C. to about 65° C., so this temperature range is preferred. Finally the temperature also affects the bubble point pressure and amount of ethylene in the liquid phase. The higher the temperature the higher the pressure needed to maintain a single phase, which increases capital cost of the manufacturing plant because of, for example, thicker vessels needed, and larger compressors to attain the higher ethylene pressure. Higher pressure also increases energy costs. Again the temperature range cited leads to moderate bubble point pressures.

FIG. 1 shows bubble point pressure vs. temperature in the range of 25° C. to 80° C., using as a solvent a typical mixture of α-olefins produced in this process with a Schulz-Flory constant of about 0.74 (see below), and at an ethylene content of 10 weight percent. In FIG. 1, at pressure above the line in the graph a single phase will be present, while at pressure below the line in the graph a liquid and a gas phase will be present. This graph is specific to this particular mixture of ingredients, but similar plots can be generated for other combinations of ingredients. Preferably the total pressure in the reactor(s) is 1.0 to about 1.5 times the bubble point pressure under those particular process conditions, more preferably 1.0 to about 1.2 times the bubble point pressure.

The amount of ethylene oligomerization catalyst used in the reaction will preferably be the maximum permitted by the cooling capacity of the reactor(s). Catalyst may be added to the first reactor only or to one or more subsequent reactors in series. Differing amounts of catalyst may be added to each reactor. The oligomerization is quite exothermic, about 100 kJ/mole of ethylene oligomerized, and as such cooling will usually be applied to the reactor(s) to maintain the desired process temperature while maintaining high volumetric productivity of the reactor(s).

In each of the reactors the temperature and/or pressure may be different. Ethylene may be added to just the first reactor, or any combination of reactors.

Cooling may be accomplished by any method known in the art. For example cooling tubes may be run through the interior of one or more of the reactors to cool the contents. Another method of cooling is to have one or more heat exchangers external to the reactors and connected to the reactors by a liquid loop to cool the reactor contents. These external heat exchangers may be typical shell and tube exchangers. They have the advantage that they may be more readily cleaned than a heat exchangers internal to the reactors, and if more than one external heat exchanger is present, one of them may be shut down for cleaning while the manufacturing process continues. The circulation through these external heat exchange loops may also help stir the reactor contents. The reactor(s) may also be jacketed with a cooling jacket. Some or all of the feeds to some or all of the reactors may be cooled to allow the sensible heat of the ingredients to (help) cool the reactor(s). If more than one reactor is used, the liquid line(s) connecting the reactors may be cooled and/or pass through heat exchangers. Any or all of these methods may be used in any combination to cool the process ingredients as needed to maintain the desired process temperature.

An important item in the capital cost of this manufacturing plant and in its cost of operation is the amount of ethylene that must be recycled in the process. Recycling of ethylene often involves flashing of the unreacted ethylene from the product stream, separation from other volatile ingredients (for example 1-butene), and recompression to feed to one or more of the reactors. Compressors and associated equipment add greatly to the capital costs and use a lot of energy.

In order to reduce the amount of recycle ethylene, the process may also comprise a "final" reactor in series without any ethylene feed (other than the ethylene dissolved in the liquid fed to the final reactor). The concentration of ethylene in the liquid exiting the final reactor will thus be lower than in the liquid entering, since some fraction of the entering ethylene has been consumed by the α-olefin forming reaction.

This final reactor may be a one phase (liquid full) final CSTR (or equivalent), or may simply be a liquid full final plug flow reactor. Plug flow reactors are well known in the art, see for instance J. I. Kroschwitz, et al., Ed., *Kirk-Othmer Encyclopedia of Chemical Technology*, 4$^{th}$ Ed., Vol. 20, John Wiley & Sons, New York, 1996, p. 1007–1059, which is incorporated by reference herein for all purposes as if fully set forth. The feed for the final reactor comes from the last liquid full reactor in the reactor train. One can maintain a single phase in the final reactor by maintaining the pressure from the previous reactor and/or lowering the temperature. Since a lower temperature results in a lower bubble point pressure, the pressure may be lowered to the bubble point of the liquid at that temperature. For example the line between the last reactor and the "final" reactor may contain a heat exchanger which lowers the temperature of the process liquid, after which the pressure on the liquid may be lowered. However it is preferred to maintain the pressure in the final reactor at the same pressure found in the previous reactor.

It is preferred that the final reactor be a plug flow reactor. Lower ethylene contents in the liquid phase exiting the final reactor are more readily obtained in a plug flow reactor than a CSTR. In essence, the final reactor increases the overall conversion of ethylene fed to the process, thereby lowering the amount of ethylene which is recycled.

Figure 2:
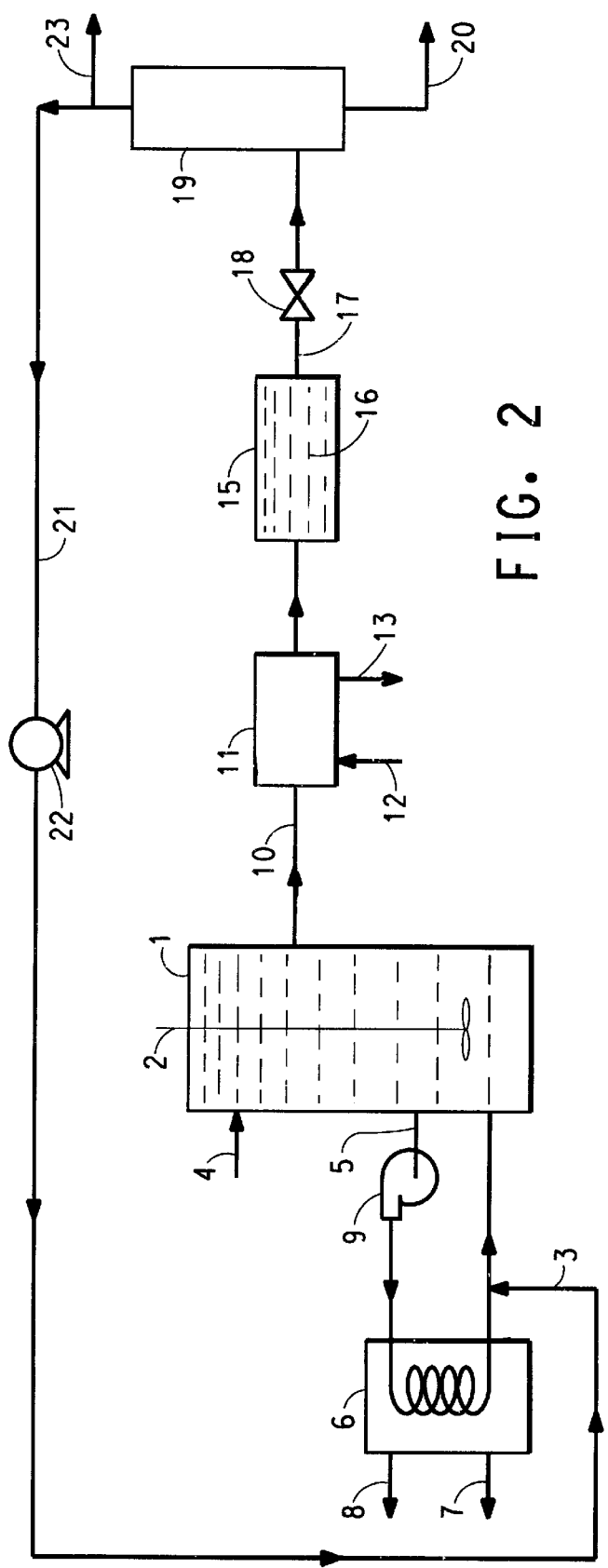
FIG. 2 shows a sample schematic diagram of a plant for manufacturing α-olefins by the present process.

FIG. 2 shows a schematic diagram of one possible configuration of an α-olefin plant manufacturing having one CSTR liquid full reactor and a final single phase plug flow reactor. A CSTR reactor 1 has an agitator 2, an ethylene feed tube 3 which feeds ethylene gas into external cooling loop 5, an oligomerization catalyst feed line 4, an external cooling loop 5 which is cooled by heat exchanger 6 which is fed heat exchange (cooling) fluid through line 7 and which exits through line 8. The liquid from 1 is circulated through 5 by pump 9. The liquid 24 exits from 1 through line 10, through shell and tube heat exchanger 11, through which coolant is circulated by lines 12 and 13, to final plug flow reactor 15. The liquid 16 in 15 exits through line 17 through pressure reduction valve 18 to gas-liquid separator 19. The liquid stream from 20, which contains the α-olefins, may then be purified, for example by fractional distillation to separate the various α-olefins. The overheads from 19, mostly ethylene, are passed through line 21 and compressor 22 (and the ethylene may also be purified, not shown) back to 1. Line 21 also has an ethylene purge line 23, to remove impurities from the recycle ethylene stream. Also not shown is possible recycle of a relatively small part of the product stream in 20 back to 1, either directly into 1, or into a holding vessel in which it is mixed with oligomerization catalyst which is fed through 4. Agitator 2 may not be necessary if the circulation from cooling loop 5 can provide enough agitation to keep the contents of 1 reasonably uniform. Addition of ethylene from 3 into 5 and then into 1 may provide additional agitation. Not all details of this plant are shown, just the major vessels and some other equipment. Arrows on the various lines indicate the direction of flow of the gas or liquid being transported.

Using the oligomerization catalysts described herein a mixture of α-olefins is obtained. A measure of the molecular weights of the olefins obtained is factor K from the Schulz-Flory theory (see for instance B. Elvers, et al., Ed. *Ullmann's Encyclopedia of Industrial Chemistry*, Vol. A13, VCH Verlagsgesellschaft mbH, Weinheim, 1989, p. 243–247 and 275–276. This is defined as:

$$K = n(C_{n+2} \text{ olefin})/n(C_n \text{ olefin})$$

wherein $n(C_n$ olefin) is the number of moles of olefin containing n carbon atoms, and $n(C_{n+2}$ olefin) is the number of moles of olefin containing n+2 carbon atoms, or in other words the next higher oligomer of $C_n$ olefin. From this can be determined the weight (mass) fractions of the various olefins in the resulting oligomeric reaction product mixture. The K factor is preferred to be in the range of from about 0.65 to about 0.8 to make the α-olefins of the most commercial interest. This factor can be varied to some extent, see for instance previously incorporated U.S. Pat. No. 6,103,946.

What is claimed is:

1. A process for the production of a linear α-olefin product, comprising the step of contacting, in a continuous stirred tank reactor, process ingredients comprising an active ethylene oligomerization catalyst composition, ethylene and a solvent, at a temperature of from about 35° C. to about 80° C., and at a pressure such that the continuous stirred tank reactor is essentially single phase liquid full, wherein the active ethylene oligomerization catalyst comprises an iron complex of a compound of the formula

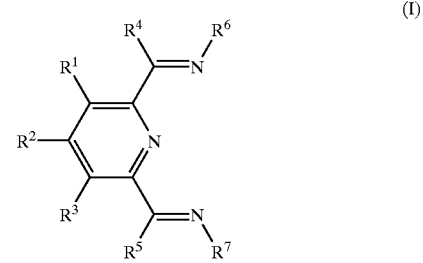

(I)

wherein:

$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently a substituted aryl having a first ring atom bound to the imino nitrogen, provided that:

in $R^6$, a second ring atom adjacent to said first ring atom is bound to a halogen, a primary carbon group, a secondary carbon group or a tertiary carbon group; and further provided that in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom.

2. The process of claim 1, wherein there are two or more of said continuous stirred tank reactors in series.

3. The process of claim 1, which additionally comprises a final reactor in series which is a final continuous stirred tank reactor or a plug flow liquid full reactor to which no additional ethylene, other than that dissolved in the liquid entering said final reactor, is added.

4. The process of claim 2, which additionally comprises a final reactor in series which is a final continuous stirred tank reactor or a plug flow liquid full reactor to which no additional ethylene, other than that dissolved in the liquid entering said final reactor, is added.

5. The process of claim 1, wherein:

$R^6$ is

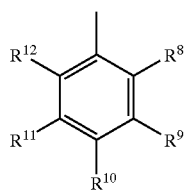
(VI)

and $R^7$ is

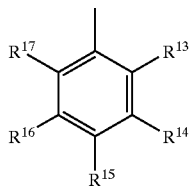
(VII)

wherein:
$R^8$ is a halogen, a primary carbon group, a secondary carbon group or a tertiary carbon group; and
$R^9$, $R^{10}$, $R^{11}$, $R^{14}$, $R^{15}$, $R^{16}$ and $R^{17}$ are each independently hydrogen, hydrocarbyl, substituted hydrocarbyl or a functional group; and
provided that:
when $R^8$ is a halogen or primary carbon group none, one or two of $R^{12}$, $R^{13}$ and $R^{17}$ are a halogen or a primary carbon group, with the remainder of $R^{12}$, $R^{13}$ and $R^{17}$ being hydrogen; or
when $R^8$ is a secondary carbon group, none or one of $R^{12}$, $R^{13}$ and $R^{17}$ is a halogen, a primary carbon group or a secondary carbon group, with the remainder of $R^{12}$, $R^{13}$ and $R^{17}$ being hydrogen; or
when $R^8$ is a tertiary carbon group, none or one of $R^{12}$, $R^{13}$ and $R^{17}$ is tertiary carbon group, with the remainder of $R^{12}$, $R^{13}$ and $R^{17}$ being hydrogen;
and further provided that any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

6. The process of claim 5, wherein:
if $R^8$ is a primary carbon group, $R^{13}$ is a primary carbon group, and $R^{12}$ and $R^{17}$ are hydrogen; or
if $R^8$ is a secondary carbon group, $R^{13}$ is a primary carbon group or a secondary carbon group, and $R^{12}$ and $R^{17}$ are hydrogen; or
if $R^8$ is a tertiary carbon group, $R^{13}$ is a tertiary carbon group, and $R^{12}$ and $R^{17}$ are hydrogen; or
if $R^8$ is a halogen, $R^{13}$ is a halogen, and $R^{12}$ and $R^{17}$ are hydrogen.

7. The process of claim 5, wherein:
$R^1$, $R^2$ and $R^3$ are hydrogen and $R^4$ and $R^5$ are methyl; and:
$R^9$, $R^{10}$, $R^{11}$, $R^{12}$, $R^{14}$, $R^{15}$, $R^{16}$ and $R^{17}$ are all hydrogen; $R^{13}$ is methyl; and $R^8$ is a primary carbon group; or
$R^9$, $R^{10}$, $R^{11}$, $R^{12}$, $R^{14}$, $R^{15}$, $R^{16}$ and $R^{17}$ are all hydrogen; $R^{13}$ is ethyl; and $R^8$ is a primary carbon group; or
$R^9$, $R^{10}$, $R^{11}$, $R^{12}$, $R^{14}$, $R^{15}$, $R^{16}$ and $R^{17}$ are all hydrogen; $R^{13}$ is isopropyl; and $R^8$ is a primary carbon group; or
$R^9$, $R^{10}$, $R^{11}$, $R^{12}$, $R^{14}$, $R^{15}$, $R^{16}$ and $R^{17}$ are all hydrogen; R is n-propyl; and $R^8$ is a primary carbon group; or
$R^9$, $R^{10}$, $R^{11}$, $R^{12}$, $R^{14}$, $R^{15}$, $R^{16}$ and $R^{17}$ are all hydrogen; $R^{13}$ is chloro; and $R^8$ is a halogen; or
$R^9$, $R^{10}$, $R^{11}$, $R^{12}$, $R^{14}$, $R^{15}$, $R^{16}$ and $R^{17}$ are all hydrogen; $R^{13}$ is trihalomethyl; and $R^8$ is a trifluoromethyl.

8. The process of claim 1, wherein an alkylaluminum compound is also present at a ratio of aluminum to iron of about 10 to about 1000.

9. The process of claim 1, wherein the reaction is run at a pressure at or above a bubble point pressure of the process ingredients, but not to exceed the critical pressure of ethylene.

10. The process of claim 9, wherein said pressure is less than twice the bubble point pressure.

11. The process of claim 9, wherein said pressure is 1.0 to about 1.5 times the bubble point pressure.

12. The process of claim 1, wherein said temperature is about 35° C. to about 75° C.

13. The process of claim 12, wherein said temperature is about 45° C. to about 65° C.

14. The process of claim 1, wherein said linear α-olefin product is typical of a process having a K factor of about 0.65 to about 0.80.

* * * * *